United States Patent [19]

Whaley

[11] Patent Number: Plant 5,422

[45] Date of Patent: Mar. 26, 1985

[54] PEACH TREE

[75] Inventor: Richard C. Whaley, Davisboro, Ga.

[73] Assignee: Washington Farms Limited, Newport Beach, Calif.

[21] Appl. No.: 497,829

[22] Filed: May 25, 1983

[51] Int. Cl.[3] ..... A01H 5/00
[52] U.S. Cl. ..... Plt./43
[58] Field of Search ..... Plt./43

*Primary Examiner*—Robert E. Bagwill
*Attorney, Agent, or Firm*—Sutherland, Asbill & Brennan

[57] ABSTRACT

A new variety of peach tree, named "June Freestone," which is very large in size, very vigorous, spreading, moderately open, vase-formed, and hardy; foliated with medium size, acuminate, lanceolate, acutely pointed, thin, dark green leaves, having a crenate, finely serrate margin and a short, thick petiole, and a very productive bearer of uniform, evenly ripening, large to medium size, nearly globose or very broadly ovate, freestone fruit having yellow skin substantially overspread with red, and firm, fine, crisp, meaty yellow flesh streaked with red.

4 Drawing Figures

ORIGIN OF THE VARIETY

The present variety of peach tree was originated in a Washington Farms orchard as an open pollinated seedling of an unnamed, unpatented variety of peach tree. The orchard is located in Georgia in the peach growing region known as the Ridge.

ASEXUAL REPRODUCTION OF THE VARIETY

When such open pollinated seedling matured as a bearing tree, and it was determined to be of commercial value, the variety was asexually reproduced by grafting on rootstock grown in the aforesaid orchard. The asexual reproduction of the variety ran true to the original tree.

SUMMARY OF THE VARIETY

The herein-claimed new and distinct variety of peach tree is very large in size, very vigorous, spreading, moderately open, vase formed, and hardy; it is foliated with medium size acuminate, lanceolate, acutely pointed, thin, dark green leaves having a crenate, finely serrate margin and a short, thick petiole; and it is a regular and very productive bearer of uniform, evenly ripening, large to medium size, nearly globose or very broadly ovate, freestone fuit having yellow skin substantially overspread with red, and having firm, fine, crisp, meaty, yellow flesh streaked with red.

The herein-claimed variety of peach tree is further and more distinctly characterized by fruit that is larger in size and earlier in the season, than Harvester or Red Globe peaches grown in the same region, also by its greater production of fruit per tree than the varieties just mentioned. The "June Freestone" fruits in the Ridge in late May, while Harvester and Red Globe trees fruit in late June or early July.

BRIEF DESCRIPTION OF THE DRAWINGS

The drawings are illustrations, by photographic reproduction in color, (A & B) of fruit of the variety; (C) of certain of the fruit cut open to expose the flesh and the stone; and (D) of a two-year old fruit-bearing tree of the variety.

DESCRIPTION OF THE VARIETY

The botanical details of this new and distinct variety of peach tree—with color definitions (except those in common color terms) referenced to "Color Kit" (National Bureau of Standards)—are as follows:

TREE

Size: Very large.
Vigor: Very vigorous.
Growth: Upright-spreading.
Density: Moderately open.
Form: Vase formed.
Hardiness: Hardy.
Production: Very productive.
Bearing: Regular bearer.

TRUNK

Size: Large.
Texture: Smooth to medium.

BRANCHES

Size: Large.
Texture: Smooth.
Color: 77.MYBr.
Lenticels:
*Number.*—Medium to numerous.
Size: Medium to medium-large.

LEAVES

Size: Medium.
*Average length.*—17.6 cm.
*Average width.*—4.0 cm.
Form: Acuminate; lanceolate; acutely pointed.
Thickness: Thin.
Color:
*Dark green.*—12794 OIG.
*Dorsal side.*—120 MyG.
*Ventral side.*—118 Deep YG.
Margin: Crenate; finely serrate.
Petiole: Short—0.8 cm; thick.
Glands: Eglandular.
Stipules: Long.—3.6 cm; twisted dehiscent.

FLOWER BUDS

Size: Medium.
Length: Medium.
Form: Obtuse, conic, plump.

Pubescence: Covers entire bud scale.

FLOWERS

Blooming period (in the ridge):
*Date of first bloom.*—Approximately February 10.
*Date of last bloom.*—Approximately March 10.
Size: Medium.
*Average length.*—3.0 cm.
*Average width.*—2.75 cm.
Form: Broad-ovate.
Appearance: Non-showy.
Color: Pink: 250 MpPk.

FRUIT

Maturity when described: Overripe.
Date of first picking: May 25 (in the Ridge).
Date of last picking: June 5 (in the Ridge).
Size: Large to medium.
*Average diameter axially.*—2½ inches.
*Average transversely in suture plane.*—2¼ inches.
Form: Uniform, symmetrical; nearly globose — very broad ovate.
Suture: Distinct, very shallow; extends from base to apex; Slight depression beyond pistil point.
Lips: Equal.
Cavity: Circular to slightly elongated in suture plane, with suture showing on one such side.
*Average depth.*—¾ inch
*Average breadth.*—⅝ inch
Apex: Short; rounded; slight fleshy tip.
Pistil point: Apical.

SKIN

Thickness: Medium.
Texture: Medium.
Tenacity: Tenacious to flesh.
Tendency to crack: None.
Down: Moderate; Medium length.
Color:
*Ground color.*—52.1. O.
*Blush.*—36. Deep rO.

FLESH

Color: 70.I.OY Streaked with red next to skin and throughout; Surface of pit cavity — red with yellow fibers
Amygdalin: Scant.
Texture: Firm; fine; crisp; meaty.
Fibers: Few; fine; tender.
Ripens: Evenly.
Flavor: Sub-acid; mild.
Aroma: Wanting.
Eating quality: Fair to good.

STONE

Type: Free; Parts from flesh smoothly.
Size: Medium.
*Average length.*—2.8 cm.
*Average breadth.*—2.3 cm.
*Average thickness.*—1.9 cm.
Form: Round to ovate.
Base: Wide.
Hilium: Narrow; oval.
Apex: Wide.
Sides: Equal; curved on both sides.
Surface: Grooves at base and apex; pits on body.
Ridges: Scattered on both sides.
Pits: On mid-section primarily.
Ventral edge: Medium suture.
Dorsal edge: Broad suture; often keeled.
Color: Beige 76.i.yBr.
Tendency to split: Very slight.

USE

Market; Dessert.

KEEPING QUALITY

Good.

SHIPPING QUALITY

Good.

The peach tree and its fruit herein described may vary in slight detail due to climatic and soil conditions under which the variety may be grown, the present description being of the variety grown in Georgia and South Carolina.

I claim:

1. A new and distinct variety of peach tree, called, "June Freestone," substantially as illustrated and described, which is very large in size, very vigorous, spreading, moderately open, vase formed, and hardy; foliated with medium size acuminate, lanceolate, acutely pointed, thin, dark green leaves having a crenate, finely serrate margin and a short, thick petiole, and a very productive bearer of uniform evenly ripening, large to medium size, nearly globose or very broadly ovate, freestone fruit having yellow skin substantially overspread with red and firm, fine, crisp, meaty, yellow flesh streaked with red; the variety being more particularly characterized, in comparison to Harvester or Red Globe varieties, by fruit that typically ripens in early June in the Ridge region of Georgia (while Harvester or Red Globe varieties ripen in late June or early July in that region), averages slightly larger in size, has fewer split pits, is rounder, more symmetrical, and more firm of flesh, and has good shipping quality.

* * * * *

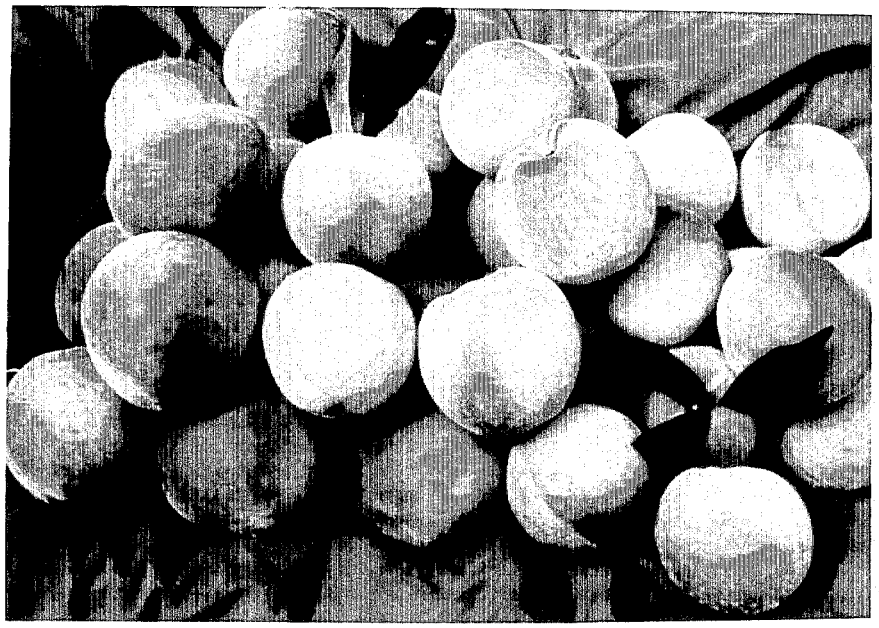
A
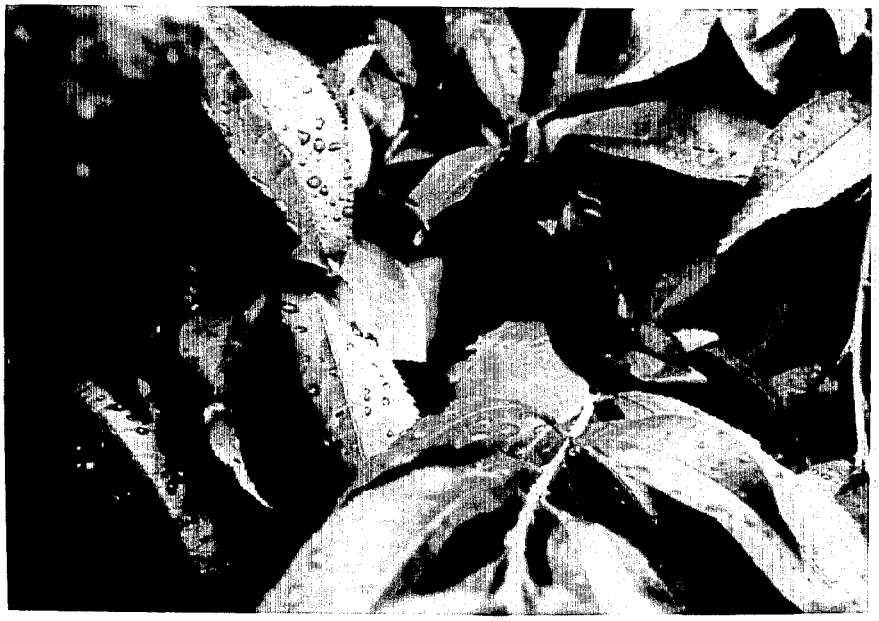
B

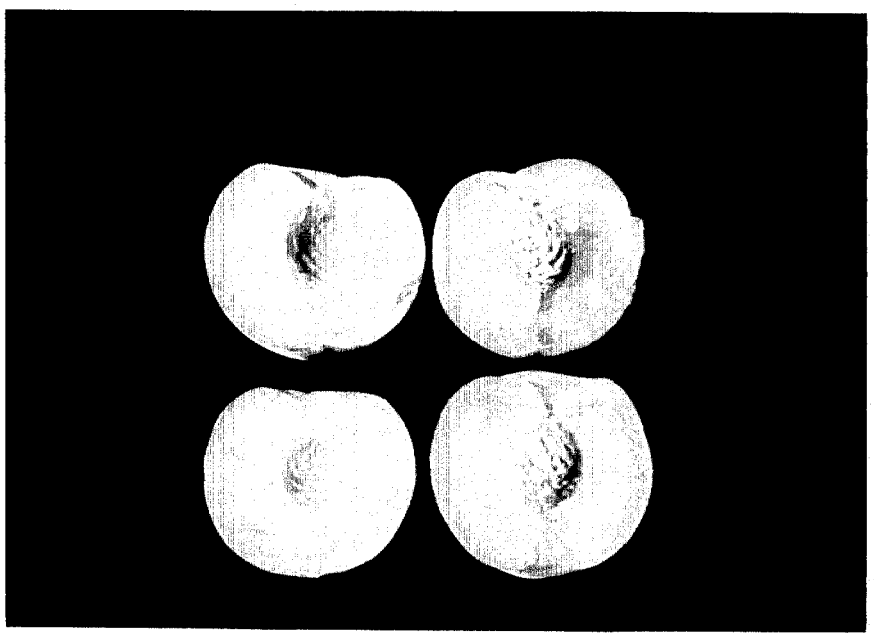
C
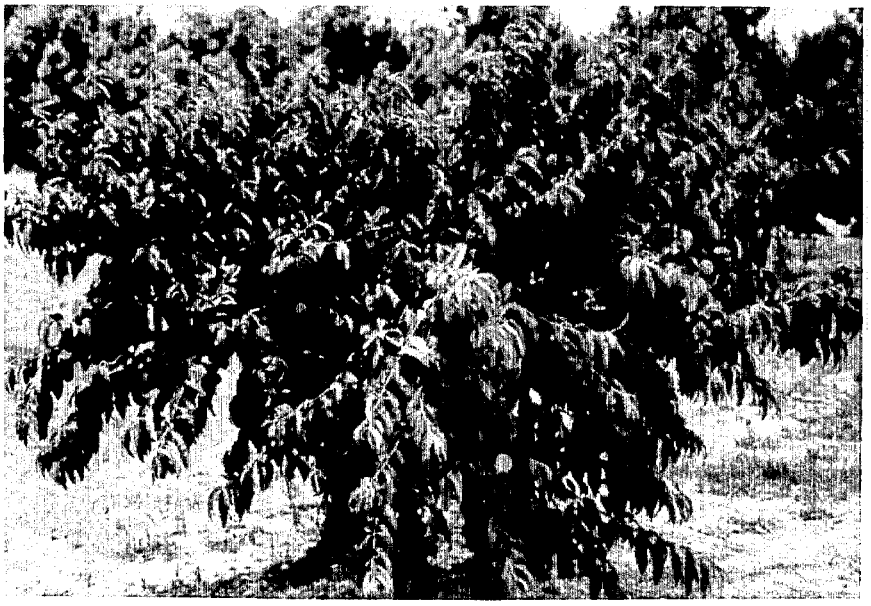
D